United States Patent [19]

Honjo et al.

[11] Patent Number: 4,816,565
[45] Date of Patent: Mar. 28, 1989

[54] INTERLEUKIN 2 RECEPTOR AND A METHOD FOR PRODUCTION THEREOF

[75] Inventors: Tasuku Honjo, Toyonaka; Akira Shimizu, Kyoto, both of Japan

[73] Assignee: Tasuku Honjo, Toyonaka, Japan

[21] Appl. No.: 895,466

[22] Filed: Aug. 11, 1986

[30] Foreign Application Priority Data

Aug. 13, 1985 [JP] Japan .................................. 60-178429
May 9, 1986 [JP] Japan .................................. 61-104886

[51] Int. Cl.$^4$ ........................ C07K 13/00; C12P 21/00
[52] U.S. Cl. ........................................ 530/351; 435/68
[58] Field of Search ........................... 530/351; 435/68

[56] References Cited

U.S. PATENT DOCUMENTS

4,578,335  3/1986  Ardal et al. ........................ 530/351

FOREIGN PATENT DOCUMENTS

162699  11/1985  European Pat. Off. .

OTHER PUBLICATIONS

Leonard et al., Nature, vol. 311, pp. 626–631, 1984.
Nikardo et al., Nature, vol. 311, pp. 631–635, 1984.
*Nature*, vol. 311, No. 5987 (Oct. 1984) pp. 631–635. T. Nikaido et al "Molecular Cloning of C NDA encoding human interleukin-2 receptor".
*Proc. Natl. Acad. Sci USA*, vol. 80, (Nov. 1983), pp. 6957–6961. W. J. Leonard et al "Characterization of the human receptor for T-cell growth factor."
*Chem. Abst.*, vol. 103, No. 25, (Dec. 23, 1985), p. 132, Abst. No. 206667b. T. A. Waldman et al "Structure, function and expression . . . Malignant lymphocytes." and *Cancer Cells*, 1985, 3 (Growth Factors transform.) 221–6.

*Primary Examiner*—Blondel Hazel
*Attorney, Agent, or Firm*—Oblon, Fisher, Spivak, McClelland & Maier

[57] ABSTRACT

Interleukin 2 receptor protein having the following properties:
(a) molecular weight: 40 to 43 kd,
(b) pI of 5.2 to 4.4,
(c) amino acid sequence (N-terminal):

Glu—Leu—Cys—Asp—Asp—Asp—Pro—Pro—Glu—Ile—
Pro—His—Ala—Thr—Phe—Lys—Ala—Met—Ala—Tyr—Lys—
Glu—Gly—Thr—Met—Leu—Asn—Cys—Glu—Cys—Lys—Arg—
Gly—Phe—Arg—Arg—Ile—Lys—Ser—Gly—Ser—Leu—Tyr—
Met—Leu—Cys—Thr—Gly—Asn—Ser—Ser—His—Ser—Ser—
Trp—Asp—Asn—Gln—Cys—Gln—Cys—Thr—Ser—Ser—Ala—
Thr—Arg—Asn—Thr—Thr—Lys—Gln—Val—Thr—Pro—Gln—
Pro—Glu—Glu—Gln—Lys—Glu—Arg—Lys—Thr—Thr—Glu—
Met—Gln—Ser—Pro—Met—Gln—Pro—Val—Asp—Gln—Ala—
Ser—Leu—Pro—Gly—His—Cys—Arg—Glu—Pro—Pro—Pro—
Trp—Glu—Asn—Glu—Ala—Thr—Glu—Arg—Ile—Tyr—His—
Phe—Val—Val—Gly—Gln—Met—Val—Tyr—Tyr—Gln—Cys—
Val—Gln—Gly—Tyr—Arg—Ala—Leu—His—Arg—Gly—Pro—
Ala—Glu—Ser—Val—Cys—Lys—Met—Thr—His—Gly—Lys—
Thr—Arg—Trp—Thr—Gln—Pro—Gln—Leu—Ile—Cys—Thr—
Gly—Glu—Met—Glu—Thr—Ser—Gln—Phe—Pro—Gly—Glu—
Glu—Lys—Pro—Gln—Ala—Ser—Pro—Glu—Gly—Arg—Pro—
Glu—Ser—Glu—Thr—Ser—Cys—Leu—Val—Thr—Thr—Thr—
Asp—Phe—Gln—Ile—Gln—Thr—Glu—Met—Ala—Ala—Thr—
Met—Glu—Thr

2 Claims, 2 Drawing Sheets

INTERLEUKIN 2 RECEPTOR AND A METHOD FOR PRODUCTION THEREOF

DETAILED DESCRIPTION OF THE INVENTION

1. Field Industrially Applicable

The present invention relates to interleukin 2 receptor (hereafter referred to as IL-2R) and a method for production thereof and more particularly, to soluble IL-2R which is released from the cortex cell and a method for production thereof. IL-2R of the present invention is highly expected to use as an agent for treatment of diseases induced by excessive immunity, etc.

2. Prior Art

IL-2R has been found as Tac antigen which is present on the cortex of T cells transformed by human adult leukemia T cell line (ATL) or human adult T cell leukemia virus (J. Exp. Med., 158, 1332–1337 (1983); Nature, 311, 631–635 (1984)) and takes a role for receiving IL-2 in the cortex of T cells and thus proliferating T cells.

The present inventors previously incorporated a gene coding for IL-2R in COS cell expression vector pKCRH 2 plasmid and transformed COS-7 cells, whereby Tac antigen, namely IL-2R, was detected on the cortex of the COS cells (Nature, 311, No. 5987, 631–635 (1984)). The entire base sequence of DNA insert inserted in pKCRH 2 plasmid is determined and the coding is presumed.

Problem Solved by the Invention

IL-2R possesses an action to scavenge IL-2 but could not be administered to the patient because IL-2R has been hitherto produced in the form bound to the cell cortex. Accordingly, an object of the present invention is to provide free IL-2R released from the cortex cell and a method for production thereof.

Means for Solving the Problem

Figure 1:
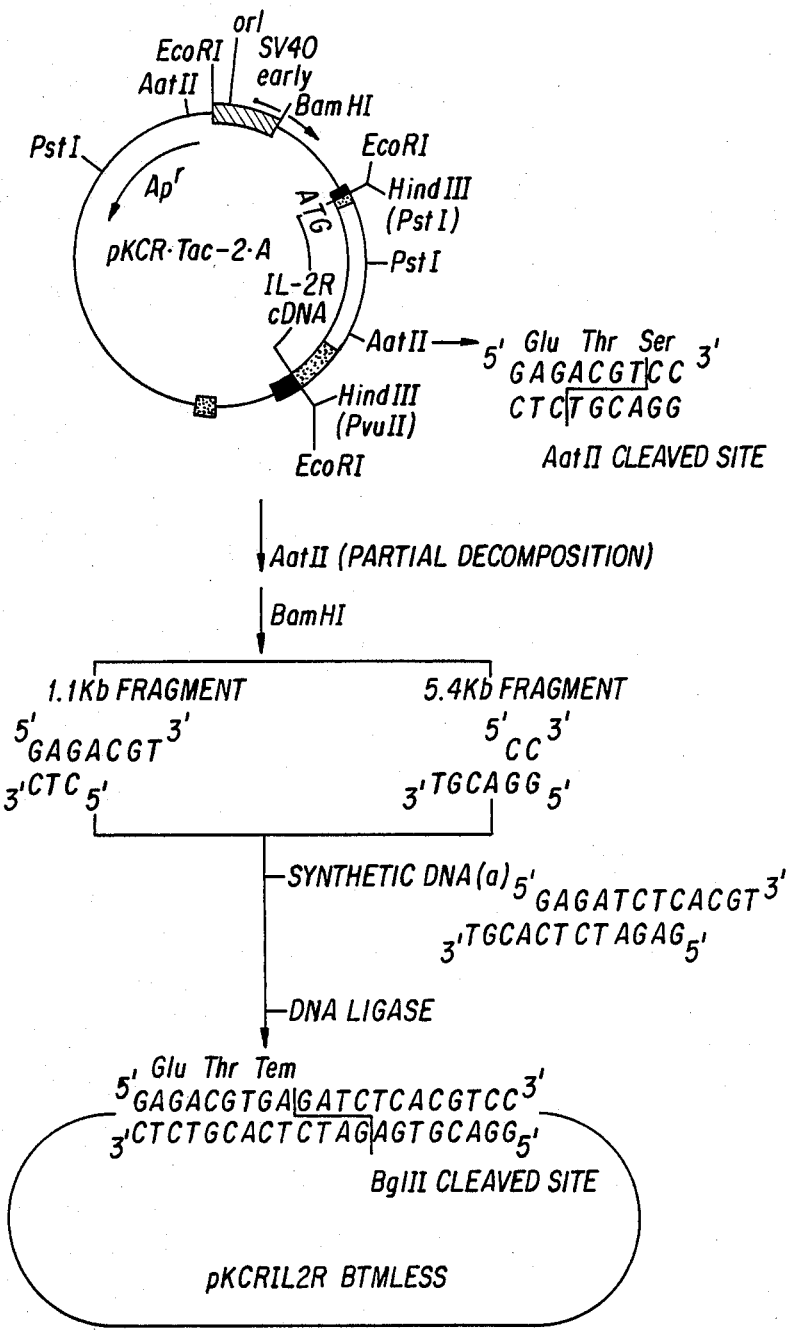
FIG. 1 illustrates the construction of pKCRIL2R BTMLESS.

As a result of extensive investigations to solve the foregoing problems, the present inventors have succeeded in producing interleukin 2 receptor released from the cell cortex by culturing an L cell or microorganism belonging to the genus Escherichia, which possesses a gene (referred to as "IL-2R gene") coding for the following polypeptide arranged to express the downstream of a promoter sequence and a vector DNA capable of proliferating in a host cell.

X—Glu—Leu—Cys—Asp—Asp—Asp—Pro—Pro—Glu—Ile—
    GAG CTC TGT GAC GAT GAC CCG CCA GAG ATC

Pro—His—Ala—Thr—Phe—Lys—Ala—Met—Ala—Tyr—
    CCA CAC GCC ACA TTC AAA GCC ATG GCC TAC

Lys—Glu—Gly—Thr—Met—Leu—Asn—Cys—Glu—Cys—
    AAG GAA GGA ACC ATG TTG AAC TGT GAA TGC

Lys—Arg—Gly—Phe—Arg—Arg—Ile—Lys—Ser—Gly—
    AAG AGA GGT TTC CGC AGA ATA AAA AGC GGG

Ser—Leu—Tyr—Met—Leu—Cys—Thr—Gly—Asn—Ser—
    TCA CTC TAT ATG CTC TGT ACA GGA AAC TCT

Ser—His—Ser—Ser—Trp—Asp—Asn—Gln—Cys—Gln—
    AGC CAC TCG TCC TGG GAC AAC CAA TGT CAA

Cys—Thr—Ser—Ser—Ala—Thr—Arg—Asn—Thr—Thr—
    TGC ACA AGC TCT GCC ACT CGG AAC ACA ACG

Lys—Gln—Val—Thr—Pro—Gln—Pro—Glu—Glu—Gln—
    AAA CAA GTG ACA CCT CAA CCT GAA GAA CAG

Lys—Glu—Arg—Lys—Thr—Thr—Glu—Met—Gln—Ser—
    AAA GAA AGG AAA ACC ACA GAA ATG CAA AGT

Pro—Met—Gln—Pro—Val—Asp—Gln—Ala—Ser—Leu—
    CCA ATG CAG CCA GTG GAC CAA GCG AGC CTT

Pro—Gly—His—Cys—Arg—Glu—Pro—Pro—Pro—Trp—
    CCA GGT CAC TGC AGG GAA CCT CCA CCA TGG

Glu—Asn—Glu—Ala—Thr—Glu—Arg—Ile—Tyr—His—
    GAA AAT GAA GCC ACA GAG AGA ATT TAT CAT

Phe—Val—Val—Gly—Gln—Met—Val—Tyr—Tyr—Gln—
    TTC GTG GTG GGG CAG ATG GTT TAT TAT CAG

Cys—Val—Gln—Gly—Tyr—Arg—Ala—Leu—His—Arg—
    TGC GTC CAG GGA TAC AGG GCT CTA CAC AGA

Gly—Pro—Ala—Glu—Ser—Val—Cys—Lys—Met—Thr—
    GGT CCT GCT GAG AGC GTC TGC AAA ATG ACC

His—Gly—Lys—Thr—Arg—Trp—Thr—Gln—Pro—Gln—
    CAC GGG AAG ACA AGG TGG ACC CAG CCC CAG

Leu—Ile—Cys—Thr—Gly—Glu—Met—Glu—Thr—Ser—
    CTC ATA TGC ACA GGT GAA ATG GAG ACC AGT

Gln—Phe—Pro—Gly—Glu—Glu—Lys—Pro—Gln—Ala—
    CAG TTT CCA GGT GAA GAG AAG CCT CAG GCA

Ser—Pro—Glu—Gly—Arg—Pro—Glu—Ser—Glu—Thr—
    AGC CCC GAA GGC CGT CCT GAG AGT GAG ACT

Ser—Cys—Leu—Val—Thr—Thr—Thr—Asp—Phe—Gln—
    TCC TGC CTC GTC ACA ACA CAA GAT TTT CAA

Ile—Gln—Thr—Glu—Met—Ala—Ala—Thr—Met—
    ATA CAG ACA GAA ATG GCT GCA ACC ATG

Glu—Thr
GAG ACG wherein X represents Met or a signal peptide having Met at the N-terminal.

The above-described base sequence is an example of genes coding for the above-described polypeptide.

The present inventors have further succeeded in producing IL-2R using such genes.

To arrange IL-2R gene to express on the downstream of the promoter sequence, in the case of L cells, the IL-2R gene is arranged on the downstream of a SV 40 initial gene promoter of a vector capable of expressing in the cells, e.g., plasmid pKCRH 2 (Nature, 307, 604–608 (1984)). In the case of L cells, it is preferred that Met which becomes a initiation codon and a signal peptide as illustrated below be arranged as X.

Asp—Ser—Tyr—Leu—Leu—Met—Trp—Gly—Leu—Leu—
    GAT TCA TAC CTG CTG ATG TGG GGA CTG CTC

Thr—Phe—Ile—Met—Val—Pro—Gly—Cys—Gln—Ala
    ACG TTC ATC ATG GTG CCT GGC TGC CAG GCA

Concretely, termination codon TAG is placed soon after threonine codon of the IL-2R gene by inserting synthetic DNA (a) phosphated at the 5'-terminal thereof shown in FIG. 1 into Aat II restriction enzyme Sal I site of IL-2R cDNA of pKCR.Tac-2.A plasmid (Nature, 311, 631-635 (1984)). Thus, pKCRIL2R BTMLESS having arranged on the downstream of SV 40 initial gene promoter, initiation condon ATG, a gene coding for a signal peptide and a gene coding for secretor IL-2R peptide is constructed (cf. FIG. 1). In the case of the microorganism belonging to the genus Escherichia, the IL-2R gene is placed on the lower part from SD sequence downstream the promoter of an expression vector of the microorganism. For example, SD sequence is placed downstream from the promoter such as trp promoter, lac promoter, PL promoter of λ phage, etc. in the vector followed by the IL-2R.

Figure 2:
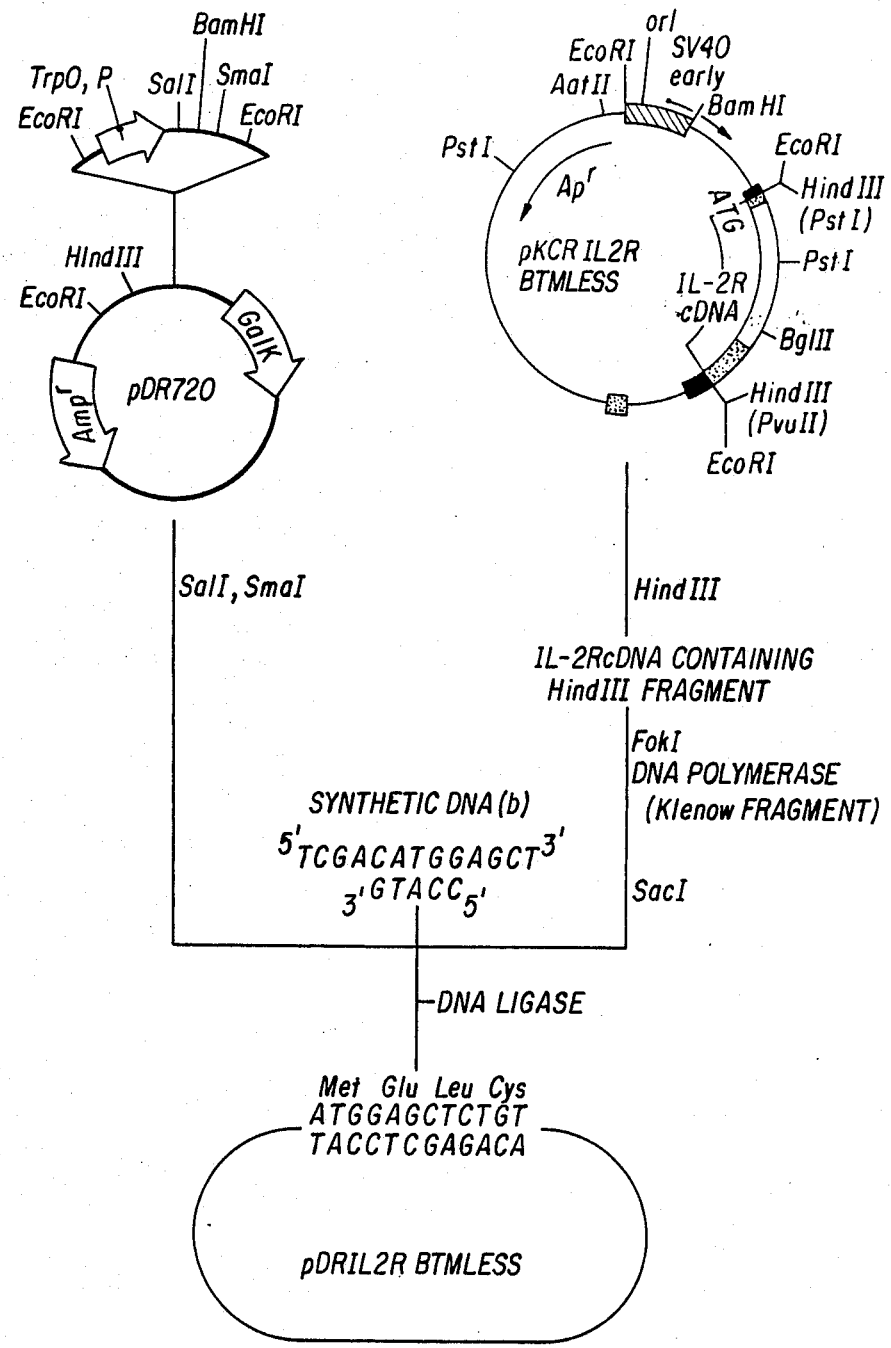
FIG. 2 illustrates the construction of pDRIL2R BTMLESS.

A specific example using trp promoter in Escherichia coli is shown below. pDR720 plasmid is cleaved by restriction enzymes Sal I and Sma I to give the cleaved straight chain plasmid. The above-described pKCRIL2R BTMLESS plasmid is cleaved by restriction enzyme Hind III to give gragment containing secretor IL-2R cDNA. After further cleaving the fragment with restriction enzyme Fok I, it is treated with DNA polymerase (Klenow fragment) and cleaved by restriction enzyme Sac I. From the reaction products, the largest fragment is recovered. The thus recovered fragment, the 5'-terminal-phosphated synthetic DNA (b) (cf. FIG. 2) and the pDR720 plasmid cleaved by restriction enzymes Sal I and Sma I are ligated with DNA ligase (FIG. 2). Thus, pDRIL2R BTMLESS having arranged SD sequence, initiation codon ATG and IL-2R gene on the downstream of trp promoter can be constructed.

To transform a host cell using vector DNA bearing the IL-2R gene, there are conventional methods for transformation shown below. In case that the host cells are L cells, there are a method for infecting DNA as calcium phosphate precipitates, a micro injection method, a method for inserting plasmid enclosed in red blood cells or ribosomes, a method for treating cells with reagents such as lysophosphatidylcholine, a method using virus vector, etc.

In case that the host cell is a microorganism belonging to the genus Escherichia, competent cells capable of incorporating DNA therein can be transformed, after recovering cells in the exponential growth phase, by the well known calcium chloride method. The efficiency of transformation can be improved in the co-presence of $MgCl_2$ or RbCl in the reaction solution after transformation. It is also possible to perform transformation after preparation of protoplast of the host cell.

Production of IL-2R protein from transformed mouse L cells by incorporating the IL-2R gene therein can be performed in accordance with a conventional method for culturing adherent cells. Namely, cultivation can be effected using a tissue culture flask such as Falcon 3024 or 3028 Flask (Falcon Labware, Div. Becton, Dickinson and Co.), while bubbling 5% $CO_2$. A roller flask such as Falcon 3027 can also be used. As medium, there may be used synthetic medium ordinarily used in tissue culture. Examples include Dulbecco's modified Eagle medium (DMEM), RPMI 1640 medium, etc. In the case of actually using these media, it is desired to supplement with 10% bovine fetal serum albumin, 100 units/ml of penicillin, 100 μg/ml of streptomycin and 2 g/l of $NaHCO_3$. The amount of IL-2R protein produced by culturing the mouse L cells varies with passage of time. To produce the IL-2R protein effectively, the following method is adopted. That is, culture is initiated in a cell density of $1 \times 10^5$/ml using DMEM medium (which contains 100 U/ml of penicillin, 100 μg/ml of streptomycin and 2 g/l of $NaHCO_3$) containing 10% FCS. When cells are dense 4 to 5 days after, the supernatant is recovered and fresh medium is supplemented followed by culturing for 3 to 4 days. After completion of the culture, the medium is recovered for quantitative assay of the amount of IL-2R protein produced. It becomes apparent that almost the same amount of the IL-2R protein is produced in the former and latter cultivation.

IL-2R can be purified from the thus obtained supernatant of the mouse L cells by affinity chromatography using IL-2-immobilized column, e.g., IL-2-Sepharose 4B or IL-2-Affi-Gel. To separate and purify in higher purity, reversed phase HPLC (high speed liquid chromatography) can be performed using an ODS column (octa decyl silane). The IL-2R protein of a single molecule using these methods has the following properties:

(a) molecular weight: 43-40 kd (SDS-PAGE)
(b) pI: 5.2 to 4.4
(c) N-terminal amino acid sequence:

Glu-Leu-Cys-Asp-Asp-Asp-Pro-Pro-Glu-Ile-

The primary structure of the N-terminal amino acid was quite identical with the amino acid structure presumed from the base sequence of the IL-2R gene.

EXAMPLE 1

As shown in FIG. 1, (1) 6 μg of plasmid pKCR.Tac-2.A (Nature, 311, 631-635 (1984)) having incorporated IL-2R cDNA in vector pKCRH2 containing a promoter for SV 40 initial gene was partially decomposed with restriction enzyme Aat II and, straight chain plasmid fragments of about 6.5 killobase (kb) were separated and recovered by agarose gel electrophoresis. The recovered fragments were 1 μg. The fragments were cleaved with restriction enzyme BamH I and, 0.35 μg of the 5.4 kb fragment and 0.07 μg of a 1.1 kb fragment were separated and recovered by agarose electrophoresis. Oligonucleotide having a sequence of $^{5'}$GAGATCTCACGT$^{3'}$ was synthesized by a DNA automatic sysnthetic machine (made by Applied Bio System Co., Ltd., Model 380A). After purifying by reverse phase HPLC, the 5'-site was phosphated with $T_4$ polynucleotide kinase. In 10 μl of a reaction solution, 0.04 picomoles each of the 5.4 kb fragment and the 1.1 kb fragment and 0.16 picomoles of the aforesaid oligonucleotide having 12 sequence were maintained at 15° C. for 1 hour. Then, the mixture was diluted to 100 μl. Ligation was further performed at 15° C. for 12 hours using $T_4$ DNA.

(2) Using 10 μl of this reaction solution, Escherichia coli HB101 was transformed in a conventional manner to give about 250 strains resistant to ampicillin. Twelve strains were optionally chosen therefrom and their plasmid DNAs were extracted. Then 5 transformants were obtained using plasmids satisfying the following 3 points that (1) the size of plasmid is about 6.5 kb, (2) the site cleaved by restriction enzyme Aat II is one, and (3) the site cleaved with restriction enzyme BgI II derived from the 12 oligonucleotides is present at the original site cleaved with restriction enzyme Aat II. The base sequence of the plasmid in the transformants was examined by the dideoxynucleotide chain termination method (Proc. Natl. Acad. Sci. U.S.A., 74, 5463 (1977)). It was confirmed that the plasmid has a base quence of pKCRIL2R BTMLESS shown in FIG. 1.

(3) From the thus obtained transformants, pKCRIL2R BTMLESS plasmid was purified by the cesium chloride equilibration centrifuge method. The purified plasmid was infected to mouse L cells (tk$^{31}$ mutant) (hereafter referred to as L cells) by the following method. That is, a suspension of $1 \times 10^5$ of L cells in 10 ml of 10% bovine fetal serum-containing Dulbecco's Eagle medium (DMEM) was charged in a Falcon 3003 dish followed by culturing at 37° C. for 20 hours in a 5% carbon dioxide gas incubator. Then, the medium was replaced by 10 ml of fresh one followed by culturing for 4 hours under the same conditions. After the incubation, 0.5 ml of Solution A (50 mM Hepes-280 mM NaCl-1.5 mN sodium phosphate buffer, pH 7.22) and 0.5 ml of Solution B (2M CaCl$_2$-10 μg pKCRIL2R BTMLESS-1 μg pBR322-herpes Tk) were supplemented to the system followed by culturing at 37° C. for 12 hours in a 5% carbon dioxide gas incubator. The culture was washed with TBS (0.137M NaCl-0.05M KCl-5.6 mM Na$_2$HPO$_4$-250 mM Tris-hydrochloride buffer (pH 7.5)) and then treated with a TBS solution containing 2.5% glycerol for 3 minutes. Immediately after the treatment, the system was washed with TBS and 10 ml of DMEM containing 10% bovine fetal serum was added thereto followed by culturing at 37° C. for 2 days in a 5% carbon dioxide gas incubator. Thereafter 10 ml of HAT medium (DMEM containing 13.6 mg/l hypoxanthine, 3.88 mg/l thymidine, 0.176 mg/l aminoputerine and 10% bovine fetal serum) was substituted for the medium followed by culturing at 37° C. for 2 days in a 5% carbon dioxide gas incubator. The substitution of the medium was carried out every 2 other days. On Day 14, 12 colonies appeares per the dish. Each colony thus appeared was transferred to a 96-cell microplate followed by culturing at 37° C. in a 5% carbon dioxide gas incubator. The incubation was performed for further 2 days after it became dense. The secretor IL-2R in the culture supernatant in each colony was identified by the following method. As a result, secretor IL-2R-producing cells BTMLESS-J and BTMLESS-Q were obtained.

ATL-derived cell line MT-1 cells, on the cortex of which many IL-2Rs are expressed can be killed by treatment with anti-IL-2R monoclonal antibody (anti-Tac antibody) and a complement. Thus, a specimen containing secretor IL-2R is reacted with antibody, MT-1 cells are added the reaction mixture and the resulting mixture is further treated with complement. If the secretor IL-2R is present in the specimen, it will bind to the antibody so that the antibody to be reacted with MT-1 cells decreases. As a result, MT-1 cells will not be killed even though they are treated with the complement. Based on this principle, a trace amount (about 0.1 ng) of the secretor IL-2R can be identified. A concrete method for identification of the secretor IL-2R is as follows. Firstly, 10 μl of a specimen or 10 μl of a dilution of the specimen with 10% bovine fetal serum-containing RPMI 1640 medium was dissolved in the same medium in a V-shaped 96-cell microplate. The solution was thoroughly mixed with 10 μl of a 1.6 ng anti-Tac antibody solution followed by allowing to stand at 0° C. for 10 minutes. A suspension of 20 μl of $5 \times 10^5$/ml MT-1 cells in the above medium was added to the mixture. After mixing, the system was allowed to stand at 0° C. for 30 minutes. After centrifuging at 800 rpm for 5 minutes, the supernatant was discarded and 20 μl of complement (15-fold dilution of rabbit newborn serum with 10% bovine fetal serum-containing RPMI 1640 medium) was added thereto and mixed followed by allowing to stand at 37° C. for 30 minutes. Then 20 μl of a 0.5% tripane blue-containing PBS solution was added to measure the count of killed cells in 200 cells.

(4) The thus produced secretor IL-2R can be stored in freezing at −20° C. Even through it is condensed by ultrafiltration (e.g., Sentricon 10), its properties are unchanged. Furthermore it can be bound to IL-2 column. Namely, 100 μl of a specimen concentrated 10 times with Sentricon 10 is adsorbed to IL-2-Sephadex 4B (containing 20 μg of IL-2) column and eluted with a 0.1M sodium citrate buffer (pH 3.0) so that the secretor IL-2R is eluted out. The eluted fraction is immediately neutralized with 1M Tris base. The thus obtained secretor IL-2R inhibited the killing effect of MT-1 cells by anti-Tac antibody and complement.

EXAMPLE 2

The culture supernatant of the mouse L cells containing IL-2R protein was concentrated 10 times using Amicon hollow fibers and applied to IL-2-Sepharose 4B column chromatography to separate from other protein contaminants. Namely, the mouse L cells were cultured in 10% FCS-containing DMEM medium (100 U/ml penicillin, 100 μg/ml streptomycin and 2 g/l NaHCO$_3$) using Falcon 3027 Roller Bottle to give 15 liters of the culture supernatant. The supernatant was concentrated 10 times using Amiconhollow fibers (molecular weight, 10,000) to make 1500 ml, which was developed in IL-2-Sepharose 4B column of a 1 ml volume (binding 1.9 mg of IL-2 per 1 ml of gel). After development of the specimen, the column was thoroughly washed with 10 ml of PBS and then with distilled water in an amount equal to the column volume. From the IL-2R-Sepharose 4B column, the IL-2R protein was eluted with 0.1M acetic acid (pH 3.1). By this procedure, IL-2R was purified about 15,000 times and the recovery rate was 75%. Further the eluted fraction of the IL-2-Sepharose 4B column was purified to high purity by reverse phase HPLC using ODS column (Yamamura Science, 4 mm×60 mm). The IL-2-Sepharose 4B column eluted fraction, 4 ml, was added to ODS column which had been equlibrated with 0.1 ml of trifluoroacetic acid (pH 2.0) and the adsorbed protein was eluted by linear density gradient of acetonitrile of 0 to 80%. IL-2 was eluted with 38 to 40% of acetonitrile. By the foregoing purification method, the IL-2R molecule could be separated and purified finally 35,000 times from 15 liters of the culture supernatant, with the recovery rate of 50%.

Molecular weight of secretor IL-2R

Using the IL-2R specimen after HPLC, the purity of this specimen was examined and the molecular weight was examined with SDS-PAGE. The specimen was added to 10% polyacryamide gel containing 0.1% SDS and electrophoresis was performed. As a result, a single band was given at a place corresponding to a molecular weight of 40 kd to 43 kd. As standard proteins, bovine serum albumin, ovalbumin, chymotripsinogen and soybean trypsin inhibitor were used.

Using the purified IL-2R, pI was determined. The specimen was added to Mono P Column (Pharmacia Fine Chemicals, Sweden) equilibrated with 25 mM bis-Tris-iminodiacetic acid (pH 7.0) followed by eluting with polybuffer 74-iminodiacetic acid (pH 4.0). It was made clear that IL-2R was eluted in a range showing pH of 5.2 to 4.4 and its isoelectric point was 5.2 to 4.4

N-Terminal structure of secretor IL-2R molecule

To determine the amino acid sequence of the secretor IL-2R protein, the purified IL-2R was introduced in Protein Sequencer (Applied Biosystem Co.). Determination of the amino acid sequence was performed in accordance with the method described in J. Biol. Chem., 193, 265-275 (1951).

It was made clear that the IL-2R protein had a molecule showing the following N-terminal structure:

Glu-Leu-Cys-Asp-Asp-Asp-Pro-Pro-Glu-Ile-

This structure was quite identical with the amino acid structure presumed from the base sequence of the IL-2R gene.

Effect

According to this invention, IL-2R released from the cell cortex which can treat diseases induced by excessive immunity, etc. by scavenging and inactivating IL-2 can be constructed.

What is claimed is:

1. Interleukin 2 receptor having the following properties:
   (a) molecular weight: 40 to 43 kd
   (b) pI of 5.2 to 4.4, and
   (c) amino acid sequence (N-terminal):

Glu—Leu—Cys—Asp—Asp—Asp—Pro—Pro—Glu—Ile—
Pro—His—Ala—Thr—Phe—Lys—Ala—Met—Ala—Tyr—Lys—
Glu—Gly—Thr—Met—Leu—Asn—Cys—Glu—Cys—Lys—Arg—
Gly—Phe—Arg—Arg—Ile—Lys—Ser—Gly—Ser—Leu—Tyr—
Met—Leu—Cys—Thr—Gly—Asn—Ser—Ser—His—Ser—Ser—
Trp—Asp—Asn—Gln—Cys—Gln—Cys—Thr—Ser—Ser—Ala—
Thr—Arg—Asn—Thr—Thr—Lys—Gln—Val—Thr—Pro—Gln—
Pro—Glu—Glu—Gln—Lys—Glu—Arg—Lys—Thr—Thr—Glu—
Met—Gln—Ser—Pro—Met—Gln—Pro—Val—Asp—Gln—Ala—
Ser—Leu—Pro—Gly—His—Cys—Arg—Glu—Pro—Pro—Pro—
Trp—Glu—Asn—Glu—Ala—Thr—Glu—Arg—Ile—Tyr—His—
Phe—Val—Val—Gly—Gln—Met—Val—Tyr—Tyr—Gln—Cys—
Val—Gln—Gly—Tyr—Arg—Ala—Leu—His—Arg—Gly—Pro—
Ala—Glu—Ser—Val—Cys—Lys—Met—Thr—His—Gly—Lys—
Thr—Arg—Trp—Thr—Gln—Pro—Gln—Leu—Ile—Cys—Thr—
Gly—Glu—Met—Glu—Thr—Ser—Gln—Phe—Pro—Gly—Glu—
Glu—Lys—Pro—Gln—Ala—Ser—Pro—Glu—Gly—Arg—Pro—
Glu—Ser—Glu—Thr—Ser—Cys—Leu—Val—Thr—Thr—Thr—
Asp—Phe—Gln—Ile—Gln—Thr—Glu—Met—Ala—Ala—Thr—
Met—Glu—Thr

2. Interleukin 2 receptor having the following amino acid sequence (N-terminal):

X—Glu—Leu—Cys—Asp—Asp—Asp—Pro—Pro—Glu—Ile—
Pro—His—Ala—Thr—Phe—Lys—Ala—Met—Ala—Tyr—
Lys—Glu—Gly—Thr—Met—Leu—Asn—Cys—Glu—Cys—
Lys—Arg—Gly—Phe—Arg—Arg—Ile—Lys—Ser—Gly—
Ser—Leu—Tyr—Met—Leu—Cys—Thr—Gly—Asn—Ser—
Ser—His—Ser—Ser—Trp—Asp—Asn—Gln—Cys—Gln—
Cys—Thr—Ser—Ser—Ala—Thr—Arg—Asn—Thr—Thr—
Lys—Gln—Val—Thr—Pro—Gln—Pro—Glu—Glu—Gln—
Lys—Glu—Arg—Lys—Thr—Thr—Glu—Met—Gln—Ser—
Pro—Met—Gln—Pro—Val—Asp—Gln—Ala—Ser—Leu—
Pro—Gly—His—Cys—Arg—Glu—Pro—Pro—Pro—Trp—
Glu—Asn—Glu—Ala—Thr—Glu—Arg—Ile—Tyr—His—
Phe—Val—Val—Gly—Gln—Met—Val—Tyr—Tyr—Gln—
Cys—Val—Gln—Gly—Tyr—Arg—Ala—Leu—His—Arg—
Gly—Pro—Ala—Glu—Ser—Val—Cys—Lys—Met—Thr—
His—Gly—Lys—Thr—Arg—Trp—Thr—Gln—Pro—Gln—
Leu—Ile—Cys—Thr—Gly—Glu—Met—Glu—Thr—Ser—
Gln—Phe—Pro—Gly—Glu—Glu—Lys—Pro—Gln—Ala—
Ser—Pro—Glu—Gly—Arg—Pro—Glu—Ser—Glu—Thr—
Ser—Cys—Leu—Val—Thr—Thr—Thr—Asp—Phe—Gln—
Ile—Gln—Thr—Glu—Met—Ala—Ala—Thr—Met—Glu—Thr wherein X is Met, as an initiation condon, and a signal peptide having the sequence:

Asp—Ser—Tyr—Leu—Leu—Met—Trp—Gly—Leu—Leu—
Thr—Phe—Ile—Met—Val—Pro—Gly—Cys—Gln—Ala

* * * * *